US009028555B2

(12) United States Patent
Hashida

(10) Patent No.: US 9,028,555 B2
(45) Date of Patent: May 12, 2015

(54) ARTIFICIAL KNEE JOINT

(75) Inventor: Masahiko Hashida, Osaka (JP)

(73) Assignee: Kyocera Medical Corporation, Osaka (JP)

( * ) Notice: Subject to any disclaimer, the term of this patent is extended or adjusted under 35 U.S.C. 154(b) by 9 days.

(21) Appl. No.: 13/992,861

(22) PCT Filed: Dec. 8, 2011

(86) PCT No.: PCT/JP2011/078437
§ 371 (c)(1),
(2), (4) Date: Jun. 10, 2013

(87) PCT Pub. No.: WO2012/077755
PCT Pub. Date: Jun. 14, 2012

(65) Prior Publication Data
US 2014/0200673 A1    Jul. 17, 2014

(30) Foreign Application Priority Data
Dec. 10, 2010  (JP) ................................. 2010-275553

(51) Int. Cl.
*A61F 2/38*   (2006.01)

(52) U.S. Cl.
CPC ............. *A61F 2/3836* (2013.01); *A61F 2/3868* (2013.01); *A61F 2/3886* (2013.01)

(58) Field of Classification Search
CPC ....... A61F 2/38; A61F 2/3836; A61F 2/3886; A61F 2/3868
USPC .......... 623/20.14, 20.21, 20.22, 20.27–20.29, 623/20.31–20.35
See application file for complete search history.

(56) References Cited

U.S. PATENT DOCUMENTS

| 4,298,992 A | 11/1981 | Burstein et al. |
| 5,879,392 A * | 3/1999 | McMinn ..................... 623/20.28 |

(Continued)

FOREIGN PATENT DOCUMENTS

| JP | 56-106648 | 8/1981 |
| JP | 2004-321810 | 11/2004 |

(Continued)

OTHER PUBLICATIONS

Extended European Search Report issued Jun. 24, 2014 in corresponding European Application No. 11847467.5.

(Continued)

*Primary Examiner* — Marcia Watkins
(74) *Attorney, Agent, or Firm* — Wenderoth, Lind & Ponack, L.L.P.

(57) ABSTRACT

An artificial knee joint comprising a femoral component and a tibial plate is provided. The femoral component includes a medial condyle, a lateral condyle, a first sliding surface for coupling the medial and lateral condyles, while leaving an opening therebetween, and a second sliding surface above the first sliding surface. The tibial plate includes a medial fossa, a lateral fossa, a post insertable into the opening, a third sliding surface which the first sliding surface contacts at a posterior surface of the post, and a fourth sliding surface which the second sliding surface contacts behind the post. The artificial knee joint is configured to move in a first sliding state in which the first sliding surface is in contact with the third sliding surface, or a second sliding state in which the second sliding surface is in contact with the fourth sliding surface, according to a flexion angle.

14 Claims, 17 Drawing Sheets

(56) References Cited

U.S. PATENT DOCUMENTS

| | | | |
|---|---|---|---|
| 2003/0023314 A1 | 1/2003 | Burstein | |
| 2004/0243245 A1 | 12/2004 | Plumet et al. | |
| 2008/0288080 A1 | 11/2008 | Sancheti | |
| 2009/0043395 A1 | 2/2009 | Hotokebuchi et al. | |
| 2009/0326666 A1* | 12/2009 | Wyss et al. | 623/20.29 |
| 2010/0292804 A1* | 11/2010 | Samuelson | 623/20.14 |

FOREIGN PATENT DOCUMENTS

| | | |
|---|---|---|
| JP | 2004-535848 | 12/2004 |
| JP | 2010-188051 | 9/2010 |
| WO | 02/083032 | 10/2002 |
| WO | 2007/007841 | 1/2007 |
| WO | 2010/108550 | 9/2010 |

OTHER PUBLICATIONS

Translation of International Preliminary Report on Patentability and written opinion of the International Searching Authority issued Jun. 12, 2013 in the corresponding International Application No. PCT/JP2011/078437.

International Search Report (ISR) mailed Jan. 10, 2012 in International (PCT) Application No. PCT/JP2011/078437.

* cited by examiner

A ⟵⟶ P

Fig.18
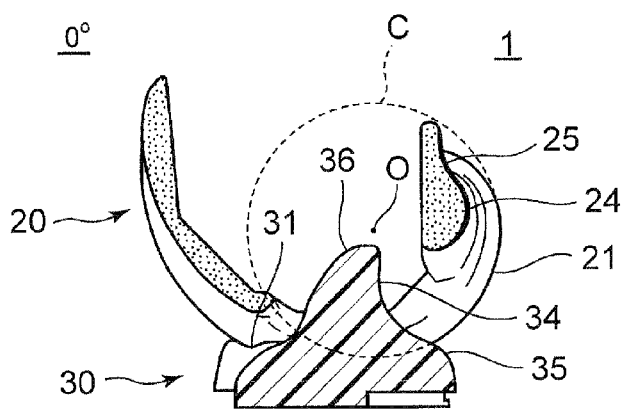
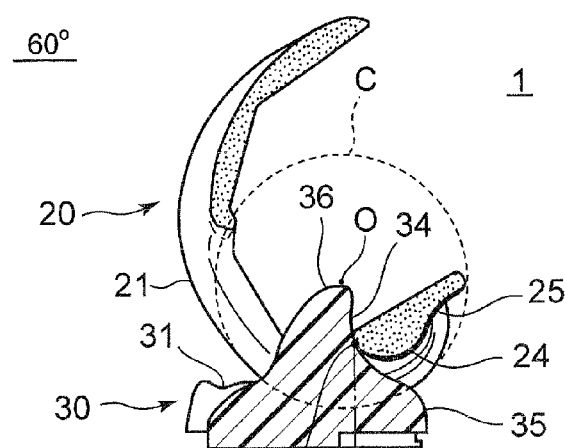
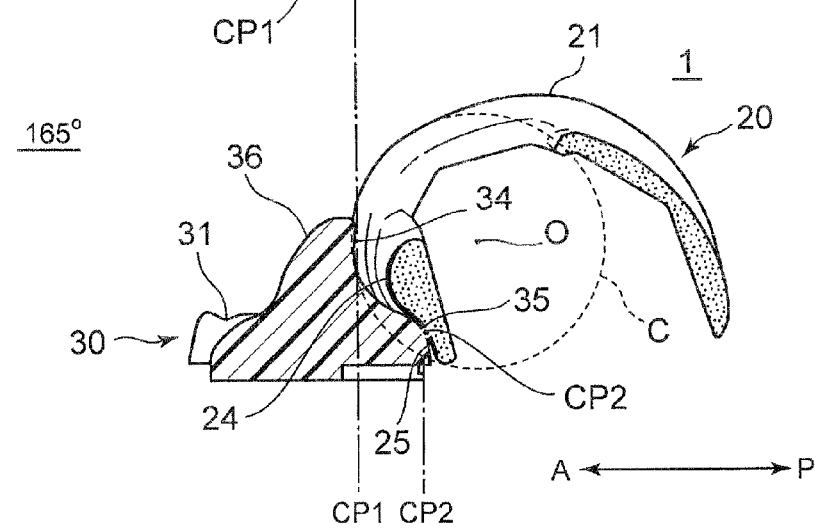

ARTIFICIAL KNEE JOINT

BACKGROUND OF INVENTION

1. Technical Field

The present invention relates to artificial knee joints, and more particularly, to an artificial knee joint that has a natural flexion movement of the knee in which the amount of rollback of a femoral component is small in slight flexion of the knee joint, and large in deep flexion thereof.

2. Background Art

When the knee joint is deformed seriously due to a degenerative knee joint disease or chronic rheumatism, a replacement surgery of an artificial knee joint is performed to restore the normal function of the knee joint.

Various proposals are made about artificial knee joints to enable the natural movement of the knee even after the replacement of the artificial knee joint. An artificial knee joint is known which is less likely to be dislocated in slight flexion, but can rotate externally in deep flexion by way of example (see, for example, JP 2010-188051 A). In the artificial knee joint, the femoral component fixed to a distal end of a femur includes a medial condyle, a lateral condyle, an opening between the medial condyle and the lateral condyle, and an elliptical spherical sliding portion for coupling posterior ends of the medial and lateral condyles together. The elliptical spherical sliding portion is adapted to slide against a tibial plate in flexion of the knee joint. The tibial plate fixed to a proximal end of a tibia includes a medial fossa for accommodating the medial condyle, a lateral fossa for accommodating the lateral condyle, a spine to be inserted into the opening, and a concave sliding surface for forming a posterior surface of the spine and slidably accommodating the elliptical spherical sliding portion.

Technical Problem

The natural knee sometimes experiences rollback according to the angle of flexion of the knee. Particularly, the natural knee has a first feature that the amount of rollback becomes small (for example, in a range of 0 to about 10 mm) in the slight flexion, and large (for example, in a range of about 10 to 30 mm) in the deep flexion, and a second feature that a ratio of rollback (ratio of the amount of rollback of the knee to the flexion angle of the knee) becomes low (for example, about +0.1 mm/degree) in the slight flexion, and becomes dramatically high (for example, +0.35 mm/degree) in deep flexion at one deflection angle or more.

In the artificial knee joint disclosed in JP 2010-188051 A, however, the rollback is caused by the flexion of the knee, which does not change the rollback ratio according to the angle of flexion of the knee.

When the amount of rollback in deep flexion is not sufficiently large, the femoral component might be in contact with the tibia in the deep flexion.

SUMMARY OF INVENTION

Accordingly, it is an object of the present invention to provide an artificial knee joint whose amount of rollback and ratio of rollback are small in slight flexion and large in deep flexion, similar to the natural knee.

Solution to Problem

An artificial knee joint according to the present invention includes a femoral component fixed to a distal part of a femur, a tibial tray fixed to a proximal part of a tibia, and a tibial plate engaged on the tibial tray. The femoral component includes a medial condyle, a lateral condyle, a first sliding surface for coupling posterior ends of the medial condyle and the lateral condyle while leaving an opening between the medial and lateral condyles, and a second sliding surface positioned above the first sliding surface. The tibial plate includes a medial fossa for accepting the medial condyle, a lateral fossa for accepting the lateral condyle, a post protruding superiorly from between the media fossa and the lateral fossa to be inserted into the opening, a third sliding surface which is formed at a posterior surface of the post and with which the first sliding surface is rotatably and slidably in contact, and a fourth sliding surface which is formed posterior to the post and with which the second sliding surface is rotatably and slidably in contact. The first sliding surface and the fourth sliding surface are convex curved surfaces. The fourth sliding surface is positioned posterior to the third sliding surface. According to a flexion angle, the artificial knee joint takes a first sliding state in which the first and third sliding surfaces are in contact with each other, or a second sliding state in which the second and fourth sliding surfaces are in contact with each other.

In order to explain the operation of the artificial knee joint of the invention, the terms used in the present specification will be defined as follows.

The term "posterior condyle" as used herein means a posterior one of the medial condyle and the lateral condyle in the femoral component. In the side view (see FIG. 17), the posterior condyle (posterior condyle 22P of the lateral condyle as shown in the drawing) can be approximated by a circle C.

The term "posterior condyle center" as used herein means the center O of the circle C by which the posterior condyle 22P is approximated.

The term "rotation center of the femoral component" as used herein means the position of the rotation center at which the femoral component rotates. The position of the rotation center is moved according to the flexion angle. Normally, the rotation center is located within a region of the femoral component.

The term "rotation radius of the femoral component" as used herein means a distance between the center O of the posterior condyle and the rotation center of the femoral component.

The term "rollback amount" as used herein means the amount of movement of the "posterior condyle center" in the anteroposterior direction (in the direction between A and P) in using the state of extension (at a flexion angle of 0°) as a basis.

The term "rollback ratio" as used herein means the rollback amount per degree of flexion angle of the knee.

The basic operation of the artificial knee joint of the present invention will be described below with reference to FIG. 18.

In the artificial knee joint of the invention, at the time of extension (at a flexion angle of 0°), a medial condyle 21 and a lateral condyle (not shown) of the femoral component 20 are in contact with a medial fossa 31 and a lateral fossa (not shown) of a tibial plate 30 (see FIG. 18(a)). This is called a "basic sliding state". When the knee is bent, for example, at a flexion angle of 60°, a first sliding surface 24 of the femoral component 20 is in contact with a third sliding surface 34 of the tibial plate 30 to become a "first sliding state" (see FIG. 18(b)). Then, for example, at a flexion angle of 165°, a second sliding surface 25 of the femoral component 20 is in contact with a fourth sliding surface 35 of the tibial plate to become a "second sliding state" (see FIG. 18(c)).

First, the rollback amount of the femoral component 20 in each sliding state will be considered.

In the basic sliding state (see FIG. 18(a)), the femoral component 20 is not substantially rolled back. In the first sliding state (see FIG. 18(b)) and the second sliding state (see FIG. 18(c)), the rollback amount of the femoral component 20 strongly depends on the contact position CP of the tibial plate with the femoral component 20. The rollback amount of the femoral component in the first sliding state depends on the contact position CP1 on the third sliding surface 34. The rollback amount of the femoral component in the second sliding state depends on the contact position CP2 on the fourth sliding surface 35. In the artificial knee joint of the invention, since the fourth sliding surface 35 is positioned posterior to the third sliding surface 34, the contact position CP2 is posterior to the contact position CP1. As a result, the rollback amount in the second sliding state is larger than that in the first sliding state.

That is, according to the artificial knee joint of the invention, the fourth sliding surface 35 is positioned posterior to the third sliding surface 34, which can make the rollback amount smaller in slight flexion, and the rollback amount larger in deep flexion.

Advantageous Effects of Invention

In the artificial knee joint of the present invention, the fourth sliding surface is positioned posterior to the third sliding surface, which makes the rollback amount smaller in slight flexion, and larger in deep flexion. Additionally, the first sliding surface and the fourth sliding surface are formed in a convex shape, which makes the rollback ratio lower in slight flexion, and higher in deep flexion. Accordingly, the artificial knee joint of the invention can operate in a similar manner to the natural knee, as compared to a conventional artificial knee joint.

BRIEF DESCRIPTION OF DRAWINGS

FIGS. 18(a) to 18(c) are cross-sectional views for explaining the operation of the artificial knee joint in the invention.

DETAILED DESCRIPTION OF EMBODIMENTS

Figure 1:
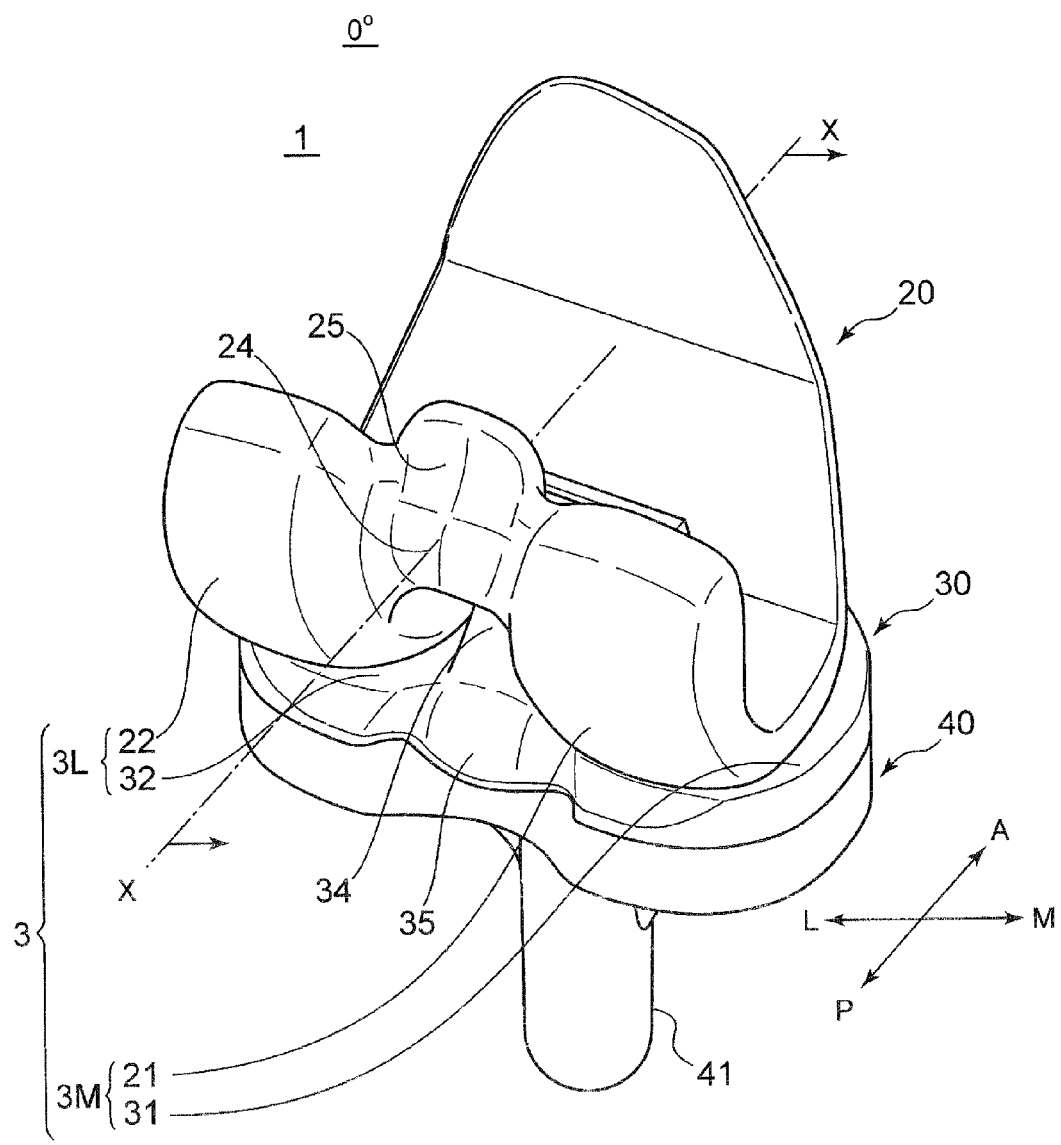
FIG. 1 is a perspective view of the artificial knee joint at a flexion angle of 0° in this embodiment.

Some embodiments of the invention will be described in detail below with reference to the accompanying drawings. In the following description, terms indicative of a specific direction or position (for example, "superior", "inferior", "right", "left", and other words containing these terms) will be used if necessary. These terms are used for easy understanding of the invention with reference to the accompanying drawings, and are not intended to restrict the technical scope of the invention by the meanings thereof. The same parts or members are indicated by the same reference characters represented in the drawings.

First Embodiment

In this embodiment, an artificial knee joint for a left knee will be described by way of example.

Figure 2:
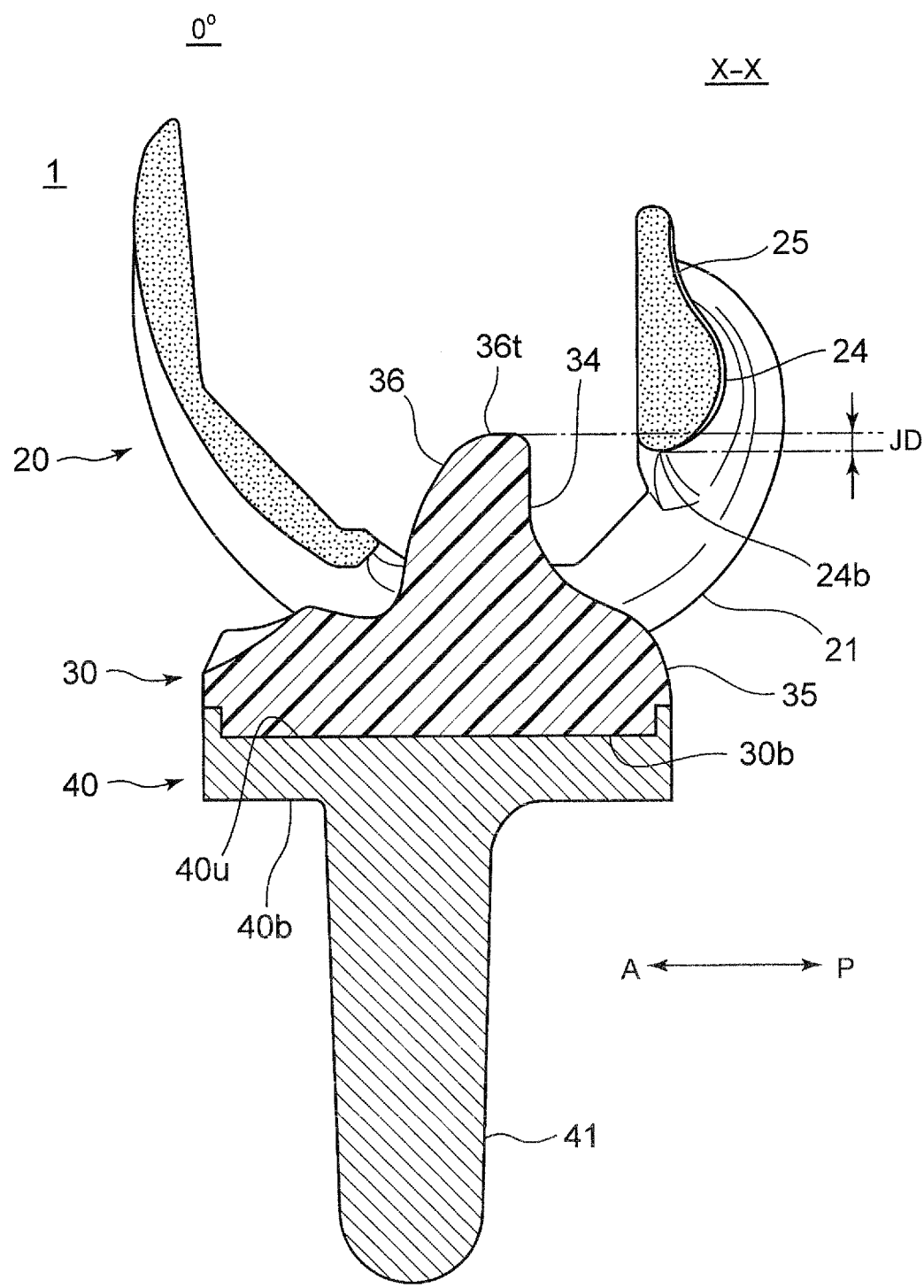
FIG. 2 is a cross-sectional view taken along line X-X of FIG. 1.
Figure 3:
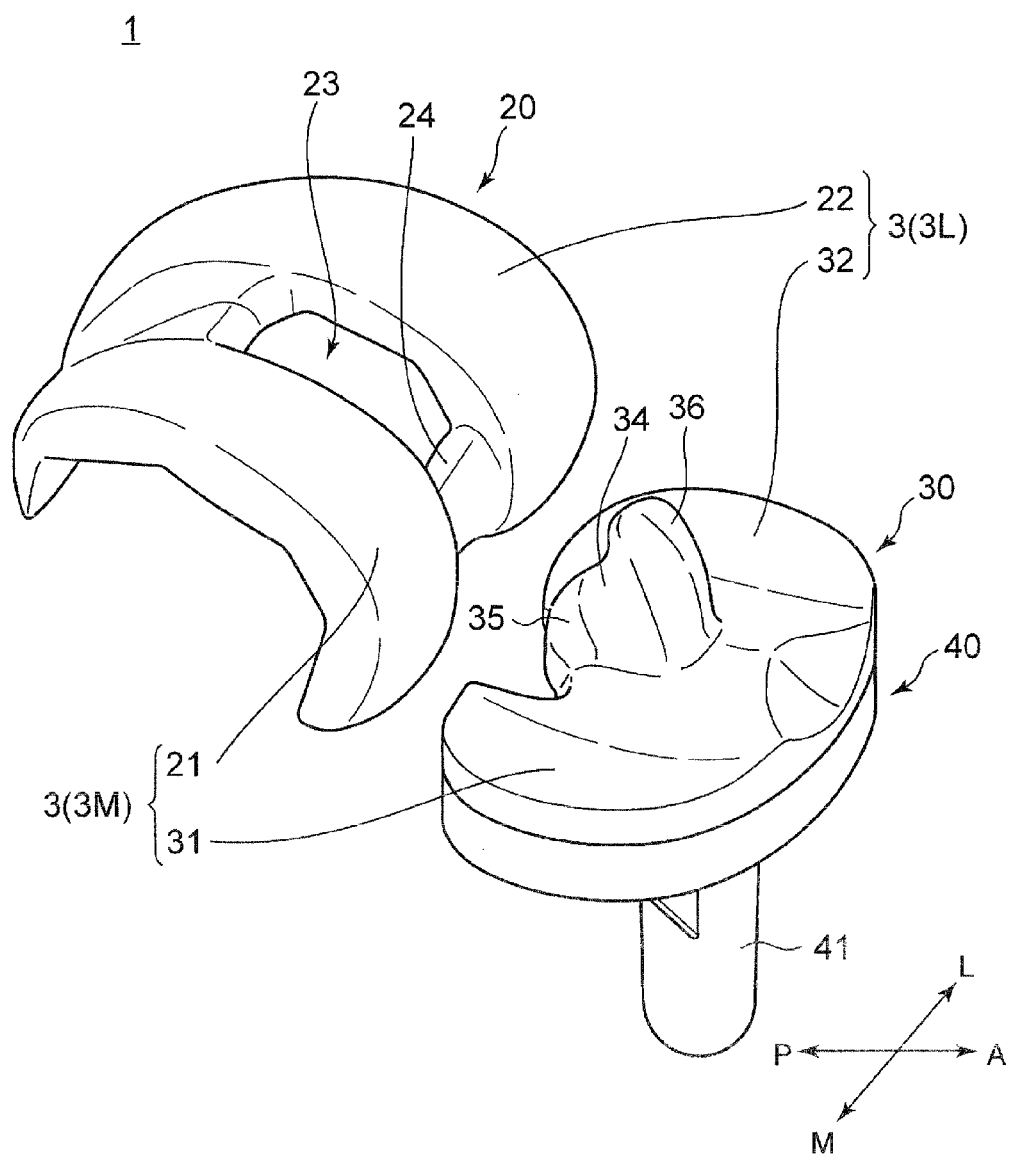
FIG. 3 is an exploded perspective view of the artificial knee joint in the first embodiment.

FIGS. 1 to 3 illustrate an artificial knee joint 1 of the invention, and the artificial knee joint 1 includes a femoral component 20 fixed to a distal part of a femur, a tibial tray 40 fixed to a proximal part of a tibia, and a tibial plate 30 engaged on the tibial tray 40.

The femoral component 20 includes a medial condyle 21, a lateral condyle 22, a first sliding surface 24 coupling posterior ends of the medial condyle 21 and the lateral condyle 22 while leaving an opening 23 between the medial and lateral condyles 21 and 22, and a second sliding surface positioned above the first sliding surface 24.

The first sliding surface 24 of the femoral component 20 is a curved convex surface.

The tibial plate 30 includes a medial fossa 31 for accepting the medial condyle 21 of the femoral component 20, a lateral fossa 32 for accepting the lateral condyle 22 of the femoral component 20, and a post 36 protruding superiorly from between the medial fossa 31 and the lateral fossa 32 to be inserted into the opening 23 of the femoral component 20. The tibial plate 30 further includes a third sliding surface 34 formed at a posterior surface of the post 36 and adapted to accept the first sliding surface 24 to rotatably and slidably contact the surface 34, and a fourth sliding surface 35 formed at the posterior side of the post 36 to slidably and rotatably contact the second sliding surface 25.

The fourth sliding surface 35 is positioned posterior to the third sliding surface 34.

The fourth sliding surface 35 of the tibial plate 30 is a convex curved surface.

The third sliding surface 34 shown in FIG. 2 is a curved surface extending substantially vertically. The third sliding surface 34 and the fourth sliding surface 35 positioned posterior thereto are continuously formed via a curved surface (concave curved surface). This arrangement can smoothly transfer from the first sliding state to the second sliding state, which can reduce a feeling of strangeness of the knee joint.

The tibial tray 40 includes a stem 41 protruding from the lower surface 40b to be inserted into the tibia. The tibial plate 30 is mounted on a superior surface 40u of the tibial tray 40.

The artificial knee joint 1 of the invention can be adapted to form three types of engagement (first engagement 3, second engagement 4, and third engagement 5).

(1) The term "first engagement 3" as used herein includes medial engagement 3M between the medial condyle 21 of the femoral component 20 and the medial fossa 31 of the tibial plate 30, and lateral engagement 3L between the lateral condyle 22 of the femoral component 20 and the lateral fossa 32 of the tibial plate 30 (see FIGS. 1 and 3). The first engagement 3 is normally formed when a flexion angle is between 0° and 165° (in some cases, between 0° and 180°). Depending on the flexion angle, the first engagement 3 may be formed only (for example, when a flexion angle is between 0° and 45°), or both the first engagement 3 and the second engagement 4 may be formed (for example, when a flexion angle is between 45° and 150°). In addition, the first engagement 3 and the third engagement 5 may be formed in some cases (for example, when a flexion angle is between 50° to 180°).

Figure 4:
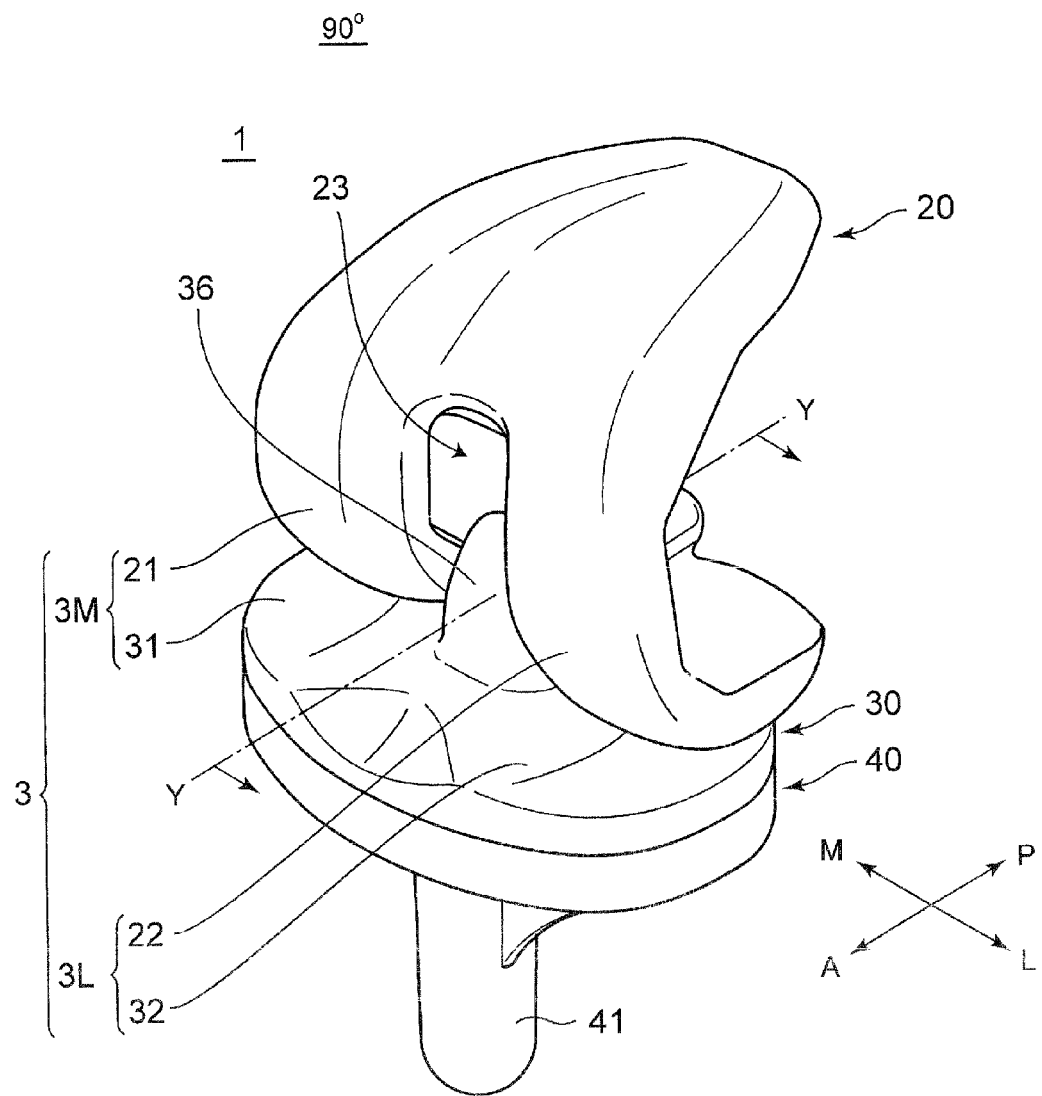
FIG. 4 is a perspective view of the artificial knee joint at a flexion angle of 90° in the first embodiment.
Figure 5:
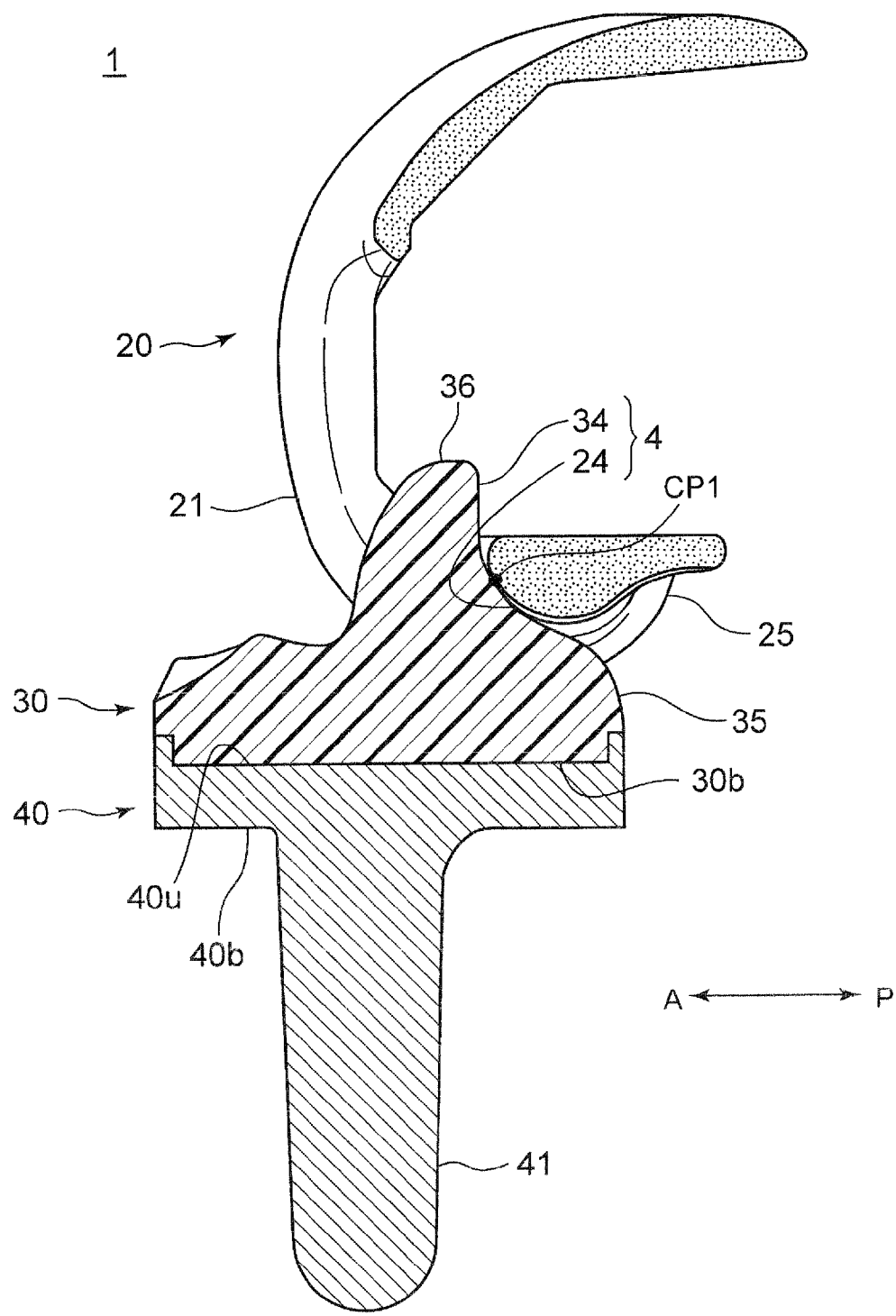
FIG. 5 is a cross-sectional view taken along line Y-Y of FIG. 4.

(2) The term "second engagement 4" as used herein is formed by contact between the first sliding surface 24 of the femoral component 20 and the third sliding surface 34 of the tibial plate 30 (see FIGS. 4 and 5). The second engagement 4 is normally formed when a flexion angle is between 45° and 150°. As mentioned above, the second engagement 4 is formed together with the first engagement 3.

Figure 6:
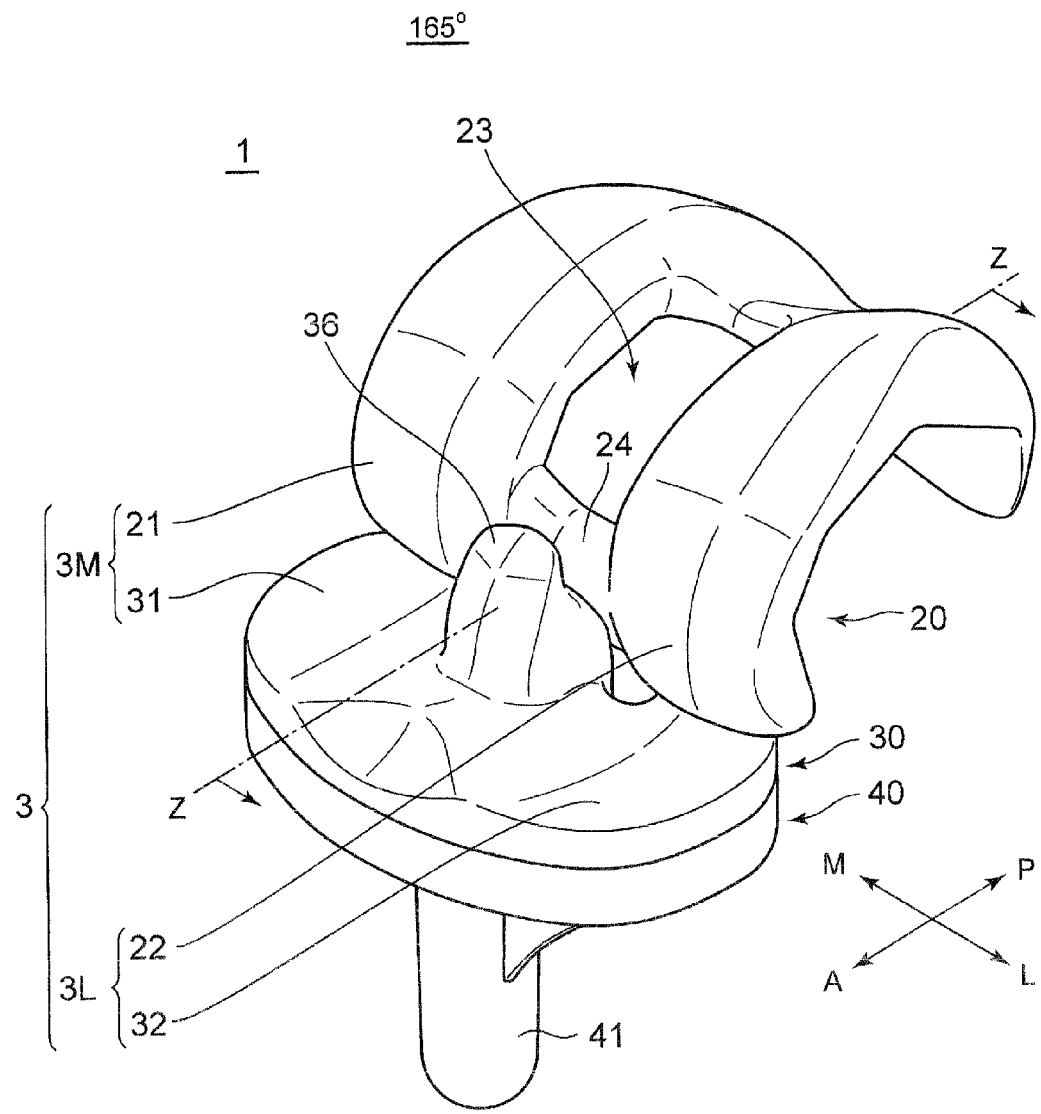
FIG. 6 is a perspective view of the artificial knee joint at a flexion angle of 165° in the first embodiment.
Figure 7:
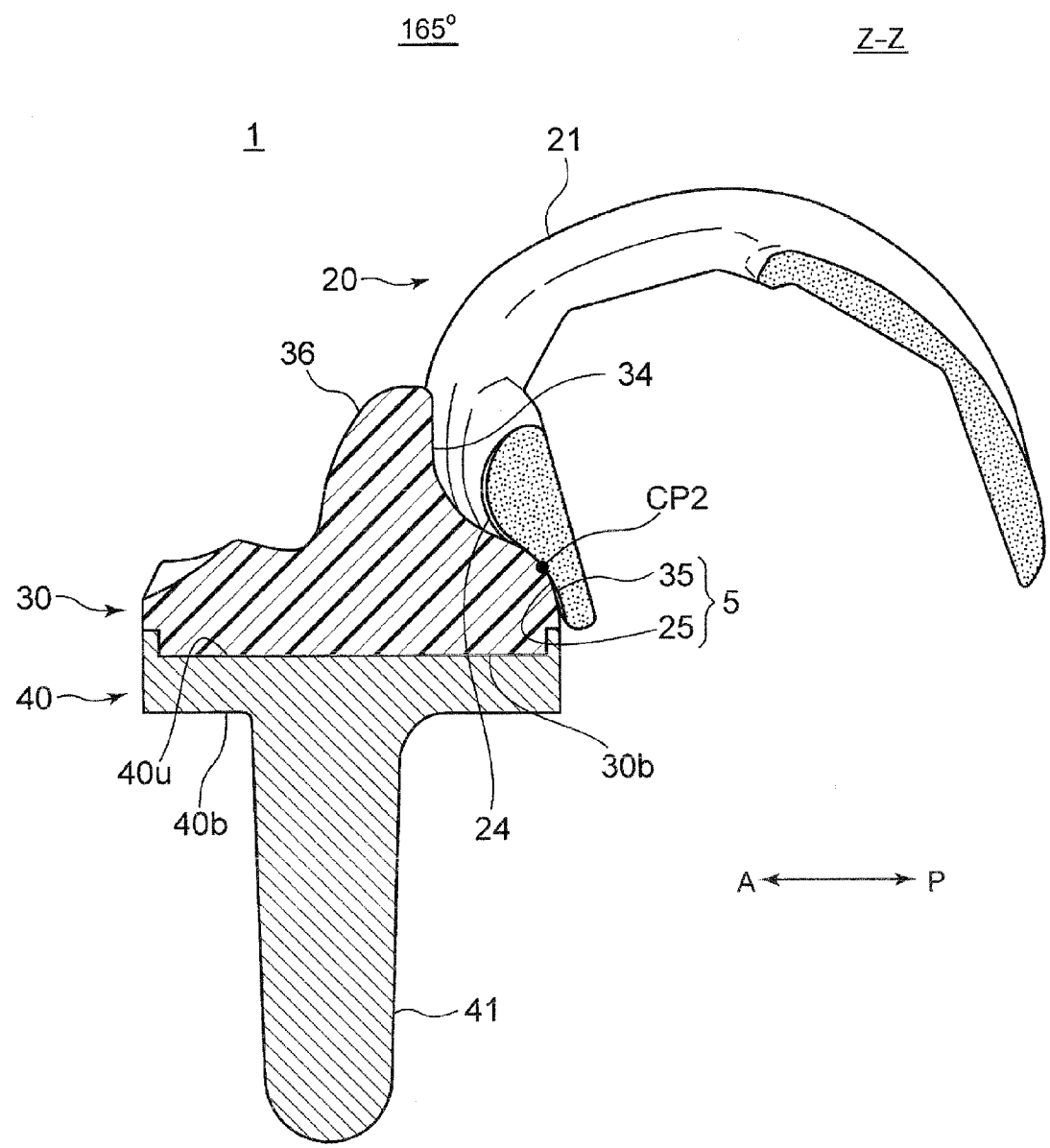
FIG. 7 is a cross-sectional view taken along line Z-Z of FIG. 6.

(3) The term "third engagement 5" as used herein is formed by contact between the second sliding surface 25 of the femoral component 20 and the fourth sliding surface 35 of the tibial plate 30 (see FIGS. 6 and 7). The third engagement 5 is normally formed when a flexion angle is between 150° and 180°. As mentioned above, the third engagement 5 may be formed together with the first engagement 3, or the third engagement 5 may be formed only.

The artificial knee joint 1 of the invention takes a state in which the second engagement 4 is formed as shown in FIGS. 4 and 5 (that is, a state in which the first sliding surface 24 and the third sliding surface 34 are in contact with each other, which is hereinafter referred to as a "first sliding state"), and another state in which the third engagement 5 is formed as shown in FIGS. 6 and 7 (that is, a state in which the second sliding surface 25 and the fourth sliding surface 35 are in contact with each other, which is hereinafter referred to as a "second sliding state"). As the flexion angle is increased, the artificial knee joint 1 transfers from the first sliding state to the second sliding state.

Next, the basic operation of the artificial knee joint in the invention will be described below.

In the basic sliding state (for example, when a flexion angle is between 0° and 45°), the medial condyle 21 and the lateral condyle 22 of the femoral component 20 are in contact with the medial fossa 31 and the lateral fossa 32 of the tibial plate 30, respectively (see FIGS. 1 to 2). In the first sliding state (for example, when a flexion angle is between 45° and 150°), the first sliding surface 24 of the femoral component 20 is in contact with the third sliding surface 34 of the tibial plate 30 (see FIGS. 4 and 5). In the second sliding state (for example, when a flexion angle is between 150° and 180°), the second sliding surface 25 of the femoral component 20 is in contact with the fourth sliding surface 35 of the tibial plate (see FIGS. 6 and 7).

The rollback amount of the femoral component 20 varies depending on states, including the basic sliding state, the first sliding state, and the second sliding state.

In the basic sliding state (see FIG. 2), there is no contact that restricts the movement of the femoral component 20 in the anteroposterior direction between the femoral component 20 and the tibial plate 30. Thus, the femoral component 20 does not move in the anteroposterior direction with respect to the tibial plate 30 (that is, the femoral component 20 is not substantially rolled back).

In the first sliding state (see FIG. 5), the femoral component 20 (first siding surface 24) is in contact with the tibial plate 30 at a contact position CP1 of the third sliding surface 34. As can be seen from FIG. 5, the femoral component 20 is prohibited from moving in the anterior direction by the tibial plate 30 (third sliding surface 34).

In the second sliding state (see FIG. 7), the femoral component 20 (second sliding surface 25) is in contact with the tibial plate 30 at a contact position CP2 of the fourth sliding surface 35. As can be seen from FIG. 7, the femoral component 20 is prohibited from moving in the anterior direction by the tibial plate 30 (fourth sliding surface 35).

In the artificial knee joint 1 of the invention, the fourth sliding surface 35 is positioned posterior to the third sliding surface 34, so that the contact position CP2 is located posteriorly with respect to the contact position CP1 (see FIGS. 5 and 7). The contact positions CP1 and CP2 are factors for determining the posterior position of the femoral component 20, whereby the position of the femoral component 20 defined by the contact position CP2 (in the second sliding state) is located posteriorly with respect to the position of the femoral component 20 (in the first sliding state) defined by the contact position CP1. The rollback amount in the second sliding state is more than that in the first sliding state.

As shown in FIGS. 10(c) to 10(h), the contact position CP1 moves over the third sliding surface 34 posteriorly as the flexion angle increases. FIGS. 10(c) to 10(e) indicate the first sliding state, FIGS. 10(f) to 10(h) indicate the transfer state from the first sliding state to the second sliding state, and FIGS. 10(i) to 10(j) indicate the second sliding state. Even in the transfer state, as the flexion angle increases, the rollback amount also increases. Since the third sliding surface 34 and the fourth sliding surface 35 are continuously formed by a curved surface (concave curved surface), the artificial knee joint can smoothly transfer from the second engagement 4 to the third engagement 5.

The transfer state desirably occurs when a flexion angle of the femoral component is between 75° and 155°.

In this way, according to the artificial knee joint 1 of the invention, the fourth sliding surface 35 is positioned posterior to the third sliding surface 34, which can make the rollback amount smaller in slight flexion, and larger in deep flexion.

The rollback ratio of the femoral component 20 varies depending on states, including the basic sliding state, the first sliding state, and the second sliding state. The rollback ratio is defined as a ratio of the rollback amount to the flexion angle (rollback amount/flexion angle). The rollback amount at a predetermined angle is the amount of movement of the "posterior condyle center" at a predetermined angle in the anteroposterior direction (A-P direction), using the state of extension (i.e. a flexion angle is 0°) as a basis.

The rotation of the femoral component 20 has been studied in detail, and the following has been found out. In the basic sliding state, the rotation center of the component 20 is positioned near the center O ($O_1$) of the posterior condyle (see FIGS. 10(a) and 10(b)).

In the basic sliding state, the femoral component 20 slides over the tibial plate 30, which does not cause the rollback. As a result, the center of the rotation of the component is substantially near the center O ($O_1$) of the posterior condyle. Thus, the rollback amount of the femoral component 20 is substantially zero (0). In contrast, in the first and second sliding states, the femoral component 20 and the tibial component 30 are in contact with each other at the contact positions CP1 and CP2, respectively, which forces the femoral component 20 to move posteriorly. Thus, the femoral component 20 is rolled back to move posteriorly. In the first sliding state, as the femoral component 20 is bent, the position CP1 moves along the third sliding surface 34 to cause the rollback (see FIGS. 10(c) to 10(h)). In the second sliding state, as the femoral component 20 is bent, the position CP2 moves along the fourth sliding surface 35. However, since the position CP2 is located posteriorly with respect to the position CP1, the rollback amount of the femoral component 20 is larger than that in the first sliding state (see FIGS. 10(h) to 10(j)).

In the present specification, the rollback ratio is defined as follows: (Rollback Ratio)=(Rollback Amount)/(Flexion Angle). In the basic sliding state, the rollback amount is substantially zero (0), and thus the rollback ratio is found to be substantially zero (0). When studying the rollback ratio between the conditions shown in FIGS. 10(d) and 10(e) in the first sliding state, a change in flexion angle of the femoral component 20 is 30 degrees, and the rollback amount corresponds to a distance between the center $O_4$ of the posterior condyle shown in FIG. 10(d) and the center $O_5$ of the posterior condyle shown in FIG. 10(e). When studying the rollback ratio between the conditions shown in FIGS. 10(h) and 10(i) in the second sliding state, a change in flexion angle of the femoral component 20 is 15 degrees, and the rollback amount corresponds to a distance between the center $O_8$ of the posterior condyle shown in FIG. 10(h) and the center $O_9$ of the posterior condyle shown in FIG. 10(i). The rollback amount in the second sliding state is more than that in the first sliding state, and the change in flexion angle in the second sliding state is small. Thus, the rollback ratio in the second sliding state is higher than that in the first sliding state.

As mentioned above, the artificial knee joint 1 of the present invention has effects of making the rollback amount and rollback ratio smaller in slight flexion and larger in deep flexion, similar to the normal knee.

Further, the artificial knee joint 1 of the invention is expected to have an effect of suppressing the dislocation of the femoral component 20 in the anterior direction (or direction A). In the artificial knee joint 1 of the invention, the post 36 of the tibial plate 30 is disposed within the opening 23 of the femoral component 20. A posterior part of the opening 23 is closed by the first sliding surface 24. When the femoral component 20 is translated in parallel to the tibial plate 30 in the anterior direction (or direction A), the tip of the post 36 is likely to interfere with the first sliding surface 24. Thus, the artificial knee joint 1 of the invention can be expected to have the effect of preventing the femoral component 20 from being moved anteriorly and from being dislocated from the tibial plate 30.

The artificial knee joint 1 of the invention can be expected to reduce influences on soft tissue (including blood vessels and nerves) of the backside of the knee.

Various measures are adopted to adjust the shape of the posterior condyle of the femoral component 20 so as to control the rotary movement and rotation movement in the deep flexion of the knee joint. Particularly, as disclosed in JP 2010-188051 A, in order to achieve the appropriate rotation movement, a spherical protrusion is provided which protrudes posteriorly with respect to the posterior condyle of the femoral component 20.

In the artificial knee joint 1 of the invention, the tibial plate 30 is provided with the fourth sliding surface 35 having a convex curved surface, instead of providing a spherical curved surface in the posterior condyle of the femoral component 20, which enables the rotation movement of the knee in the deep flexion. Thus, the protrusion protruding posteriorly from the femoral component 20 becomes smaller, which can effectively reduce the influences on the soft tissue of the backside of the knee (particularly, influences in extension).

The artificial knee joint 1 of the invention is expected to improve the stability of the first engagement 3.

The tibial plate 30 is provided with the third sliding surface 34 and the fourth sliding surface 35. The fourth sliding surface 35 does not act in the first sliding state (for example, when a flexion angle is between 45° and 150°). The size (length) of the fourth sliding surface 35 in the anteroposterior direction (A-P direction) and the size (height) thereof in the superior-inferior direction are preferably small such that the component 20 is not in contact with the fourth sliding surface until the flexion angle of 150°. Thus, areas for forming the medial fossa 31 and the lateral fossa 32 of the tibial plate 30 can be widely secured, which can effectively improve the stability of the first engagement 3.

The artificial knee joint 1 of the invention has the low rollback ratio in slight flexion and the high rollback ratio in deep flexion, similar to the natural knee joint. Specifically, in the normal knee joint, a boundary at which the knee joint transfers from a range of flexion angles (zone 1) having a low roll back ratio to a range of flexion angles (zone 2) having a high roll back ratio is in a range of 75° to 155°. Thus, in the invention, the boundary at which the artificial knee joint transfers from zone 1 to zone 2 is preferably in a range of 75° to 155°. In the graph obtained by plotting the rollback amounts against the flexion angle (for example, in FIG. 13), the rollback ratio corresponds to a slope of the graph. In other words, the flexion angle at which the slope (rollback ratio) of an increase in rollback amount of the femoral component 1 changes is preferably in a range of 75° to 155°.

The "flexion angle at which a slope is changed" can be obtained by approximating zone 1 and zone 2 with the respective straight lines in the graph and by determining an intersection point between these straight lines.

The third sliding surface 34 of the tibial plate 30 preferably has a shape corresponding to that of the first sliding surface 24 of the femoral component 20. Specifically, the first sliding surface 24 has a convex curved surface, and thus the third sliding surface 34 has a concave curved surface. Thus, when the second engagement 4 is formed, the area of contact between the first sliding surface 24 and the third sliding surface 34 is increased, which can reduce abrasion of the first sliding surface 24 and the third sliding surface 34 (particularly, the third sliding surface 34).

By way of example of a combination of the first sliding surface 24 and the third sliding surface 34, a part of the first sliding surface 24 of the femoral component 20 is formed of a cylindrical member having an axis in the medial-lateral direction (M-L direction), and the third sliding surface 34 is formed as a curved surface to accept the cylindrical member. In this example, the rotation movement is restricted while the second engagement 4 (for example, when a flexion angle is between 45° and 150°) is formed. This example is suitable for patients who are worried about the stability of the knee joint, including a patient whose knee tendon is cut, and an elderly person whose knee tendon is weak.

The shape of each of the first sliding surface 24 and the third sliding surface 34 is not limited to the description above, and can have any shape as long as the first sliding state can be appropriately achieved.

The second sliding surface 25 of the femoral component 20 preferably has a shape corresponding to the fourth sliding surface 35 of the tibial plate 30. Specifically, the fourth sliding surface 35 has a convex curved surface, and thus the second sliding surface 25 has a concave curved surface. Thus, when the third engagement 5 is formed, the area of contact between the second sliding surface 25 and the fourth sliding surface 35 is increased, which can reduce abrasion of the second sliding surface 25 and the fourth sliding surface 35 (particularly, the fourth sliding surface 35).

Specifically, the second sliding surface 25 of the femoral component 20 preferably is a spherical concave curved surface, and the fourth sliding surface 35 of the tibial plate 30 preferably is a spherical convex curved surface. Thus, when the third engagement 5 is formed, the knee joint can rotate.

The term "spherical concave curved surface" as used herein indicates a curved surface with the concave shape viewed in both a sagittal section and a horizontal section, and includes various curved surfaces, such as an inner surface of a sphere, or an inner surface of an elliptical sphere. The term "spherical convex curved surface" as used herein indicates a curved surface with the convex shape viewed in both a sagittal section and a horizontal section, and includes various curves surfaces, such as an outer surface of a sphere, or an outer surface of an elliptical sphere.

Figure 8:
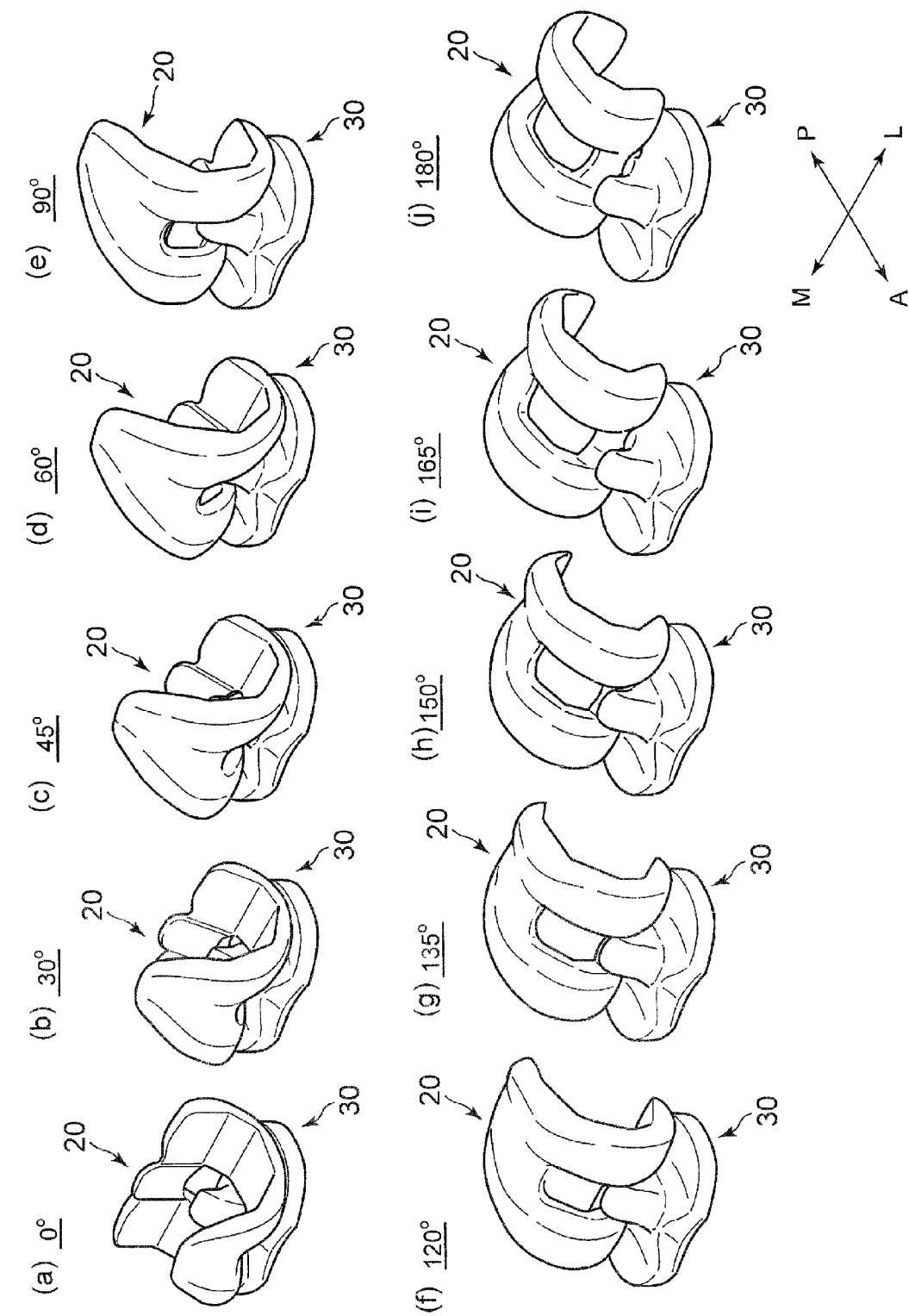
FIGS. 8(a) to 8(j) are perspective views of the artificial knee joint at various flexion angles in the first embodiment.
Figure 9:
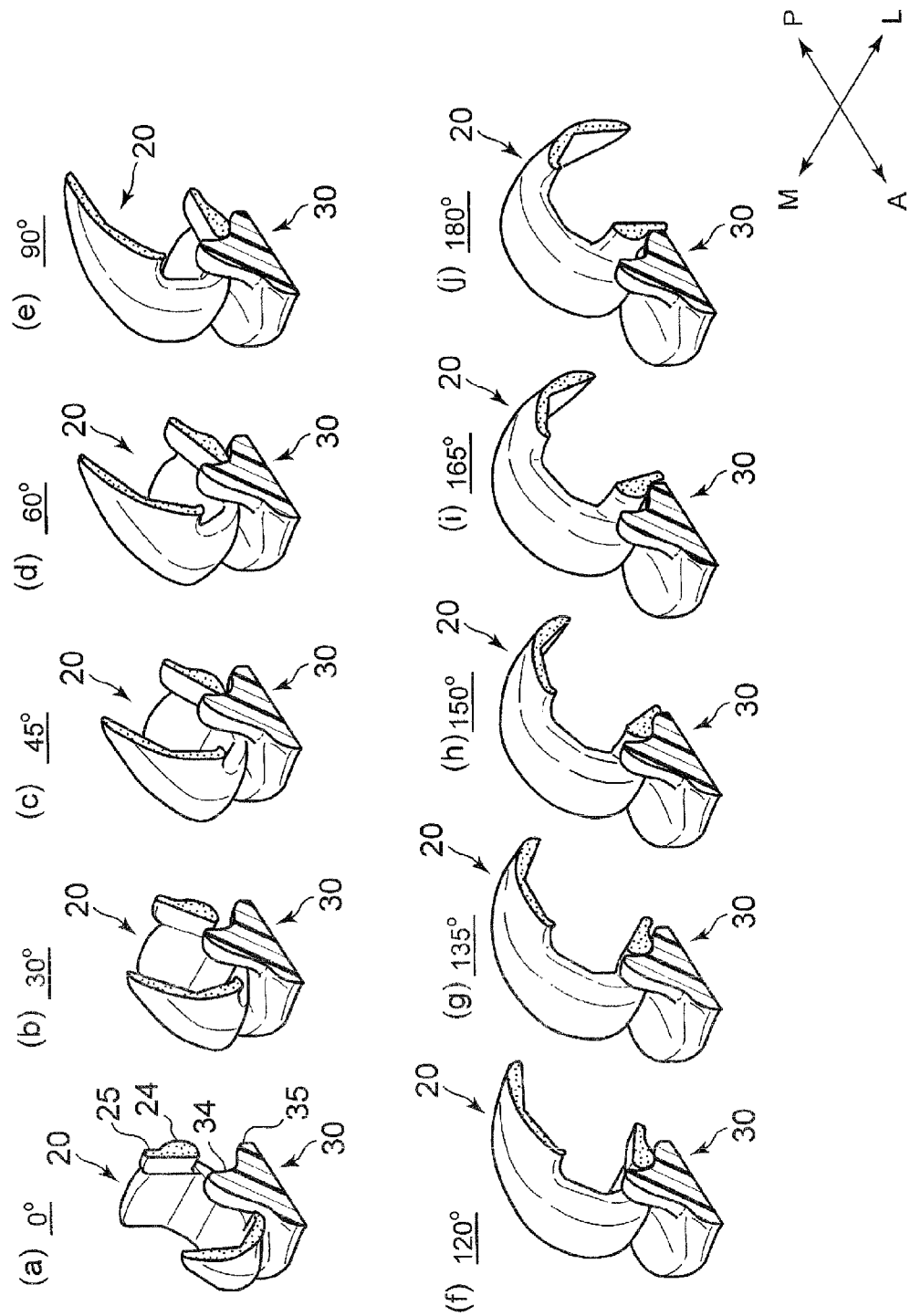
FIGS. 9(a) to 9(j) are partial cross-sectional perspective views of the artificial knee joint at various flexion angles in the first embodiment.
Figure 10:
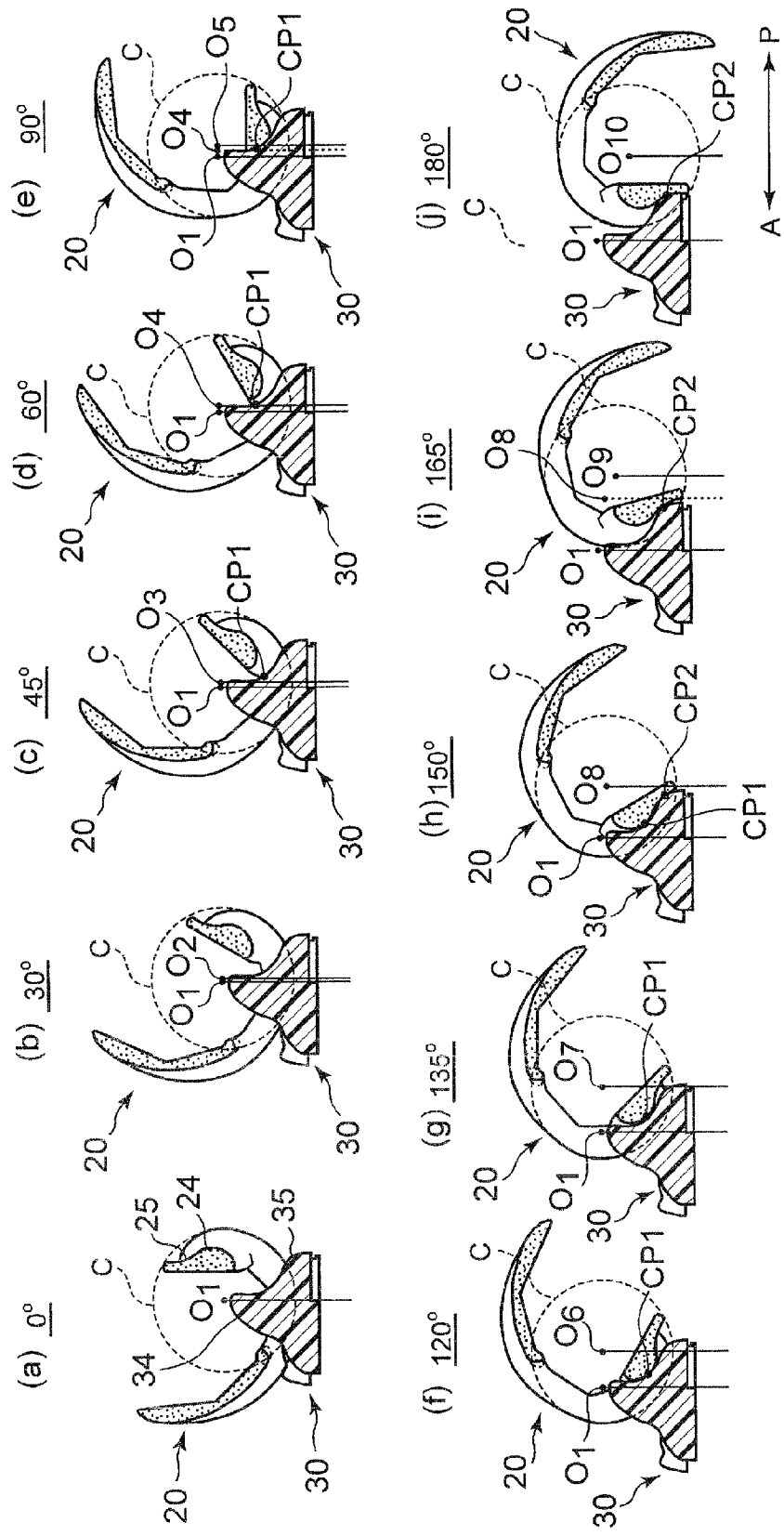
FIGS. 10(a) to 10(j) are cross-sectional views of the artificial knee joint at various flexion angles in the first embodiment.

Next, the change of the artificial knee joint 1 accompanied by the change in flexion angle will be described in detail below with reference to FIGS. 8 to 10.

(1) In Extension to Slight Flexion (Flexion Angle of 0° to 45°, see FIGS. 8(a) to 8(c), 9(a) to 9(c), and 10(a) to 10(c))

The first engagement 3 is formed (which includes a medial engagement 3M between the medial condyle 21 of the femoral component 20 and the medial fossa 31 of the tibial plate 30, and a lateral engagement 3L between the lateral condyle 22 of the femoral component 20 and the lateral fossa 32 of the tibial plate 30).

(2) In First State (Flexion Angle of 45° to 150°, see FIGS. 8(c) to 8(h), 9(c) to 9(h), and 10(c) to 10(h))

The above first engagement 3, and the second engagement 4 (comprised of a first convex curved portion 24 of the femoral component 20 and a second concave curved portion 34 of the tibial plate 30) are formed together. In the second engagement 4, the first convex curved portion 24 of the femoral component 20 is in contact with the second concave curved portion 34 of the tibial plate 30, which prevents the dislocation of the femoral component 20 in the anterior direction A.

Preferably, when the first sliding state is kept at the flexion angle of 45° to 150°, the movement of the artificial knee joint can preferably be similar to the movement of the natural knee joint.

(3) In Second State (Flexion Angle of 150° to 180°, see FIGS. 8(h) to 8(j), 9(h) to 9(j), and 10(h) to 10(j))

The artificial knee joint is transferred from the second engagement 4 to the third engagement 5 (between the first concave curved portion 25 of the femoral component 20 and the second convex curved portion 35 of the tibial plate 30). When the femoral component 20 is offset posteriorly in the direction P, the first engagement 3 is also released. However, when the artificial knee joint 1 rotates, one of the medial engagement 3M and the lateral engagement 3L in the first engagement 3 is formed again.

Preferably, when the second sliding state is kept at the flexion angle of 150° to 180°, the movement of the artificial knee joint can preferably be similar to the movement of the natural knee joint.

Figure 11:
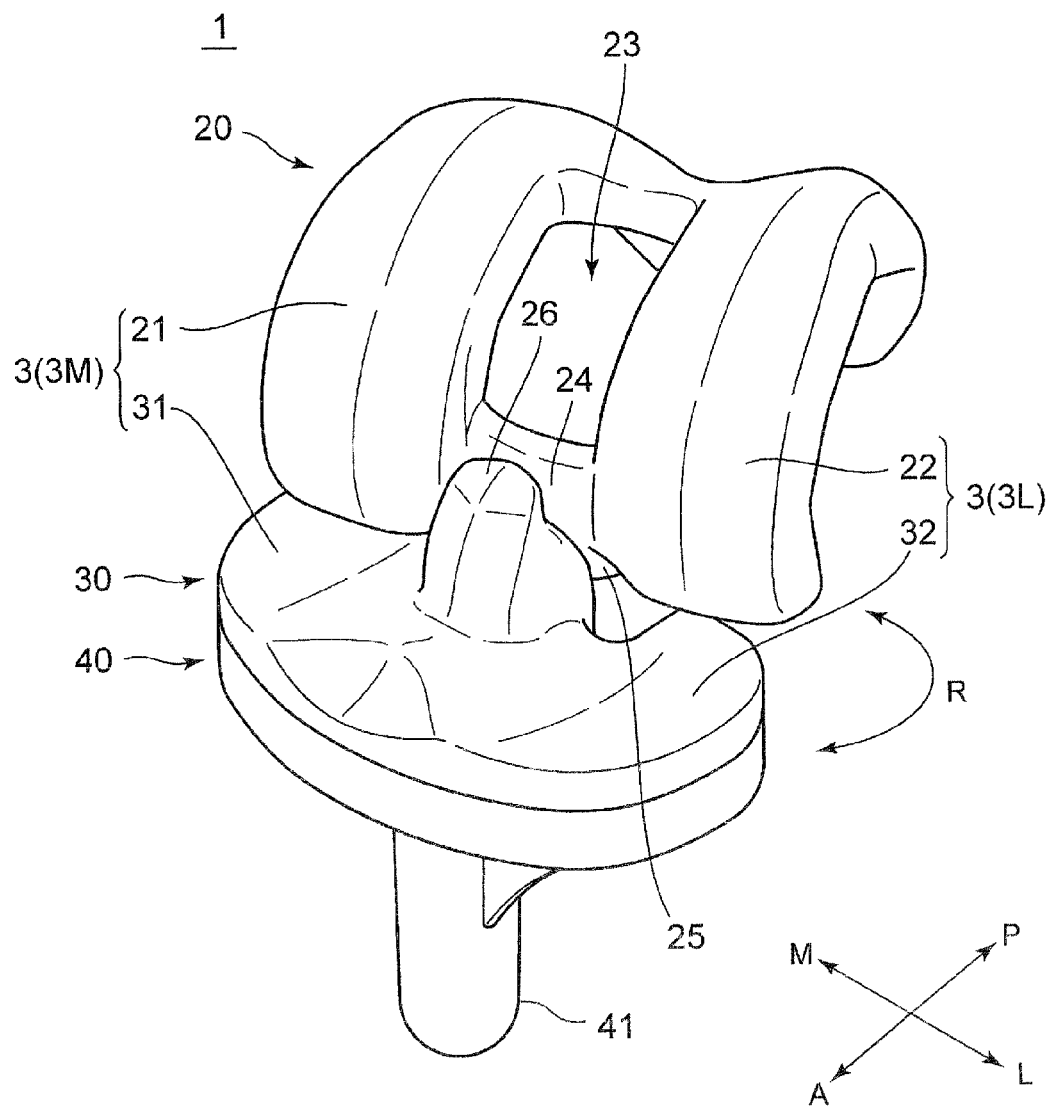
FIG. 11 is a perspective view of the artificial knee joint at a flexion angle of 165° and a rotation angle of 25° in the first embodiment.

FIG. 11 indicates the artificial knee joint 1 at the flexion angle 165° and the rotation angle of 25°. The femoral component 20 externally rotates in the direction of arrow R with respect to the tibial plate 30 as a basis. Thus, in the second state, the medial engagement 3M is formed between the medial condyle 21 and the medial fossa 31. In this way, the second state creates synergy between the offset of the femoral component 20 and the rotation of the femoral component 20 to cause the contact (the other being in non-contact state) of one of the medial engagement 3M (engagement between the medial condyle 21 and the medial fossa 31), and the lateral engagement 3L (engagement between the lateral condyle 22 and the lateral fossa 32). Thus, the knee joint after the rotation can be stabilized while keeping flexibility in rotation in the second state.

Figure 12:
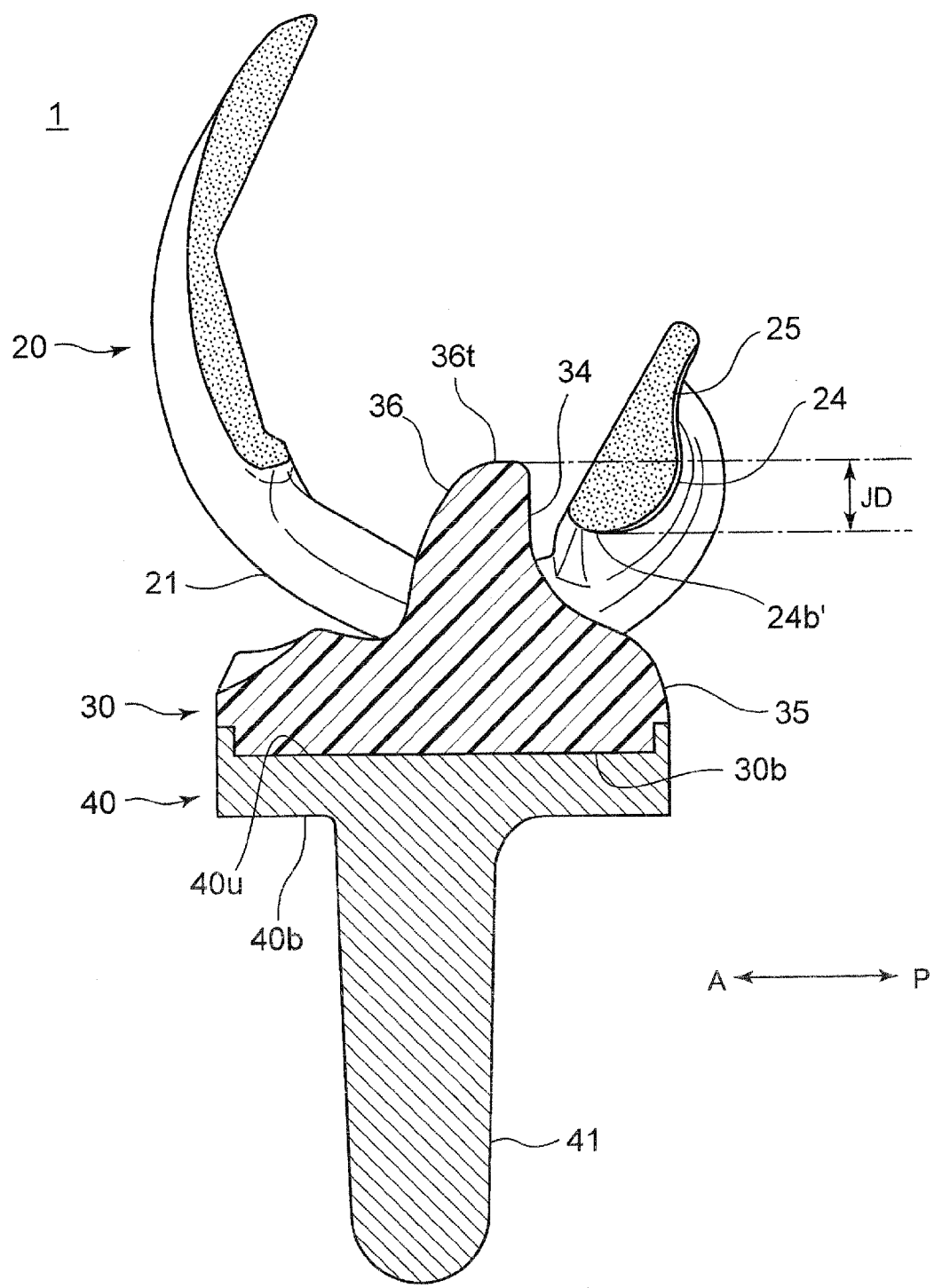
FIG. 12 is a cross-sectional view of the artificial knee joint at a flexion angle of 30° in the first embodiment.

In order to reproduce the natural movement of the knee joint, it is desirable to engage a post with a cam at a smaller flexion angle to thereby control the rollback amount. The flexion angle at which the knee joint is subjected to a load in walking is about 30°. At about 30°, it is desirable for the artificial knee joint to have a high resistance to dislocation. As shown in FIG. 12, at the flexion angle of 30°, when an inferior end 24b of the first convex curved portion 24 is located under a superior end 36t of the post 36, a jumping distance JD can be positive at the flexion angle of 30°.

The term "jumping distance" as used herein means a "height" of a barrier that the femoral component 20 has to overcome in dislocation of the knee in the anterior direction. In the artificial knee joint 1 of the invention, the jumping distance corresponds to a difference in height between the inferior end 24b of the first convex curved portion 24 and the superior end 36t of the post 36.

As shown in FIG. 12, when the superior end 36t of the post 36 is positioned above the inferior end 24b of the first convex curved portion 24, there is a barrier that the femoral component 20 overcomes in dislocation. When there is the barrier, the jumping distance JD is set to a positive value (JD>0) (hereinafter referring to as a "positive jumping distance").

As shown in FIG. 12, the jumping distance JD is set positive, which can prevent the dislocation of the femoral component 20 anteriorly at an angle of 30°.

As mentioned above, in the artificial knee joint 1 of the invention, the post 36 of the tibial plate 30 is disposed in the opening 23 of the femoral component 20, which can prevent the femoral component 20 from moving in the anterior direction to be dislocated from the tibial plate 30. As can be seen from FIG. 10, the jumping distance JD is large in deep flexion, so that the artificial knee joint 1 has a greater effect of preventing the dislocation. In contrast, the jumping distance JD is small (or the jumping distance JD becomes negative in some cases) in slight flexion (in particular, when a flexion angle is 0°), so that the artificial knee joint 1 has a smaller effect of preventing the dislocation (or never has the effect).

In general, no force is applied to move the femoral component 20 in the anterior direction at the flexion angle of 0°, which is not problematic to normal patients. As shown in FIG. 1, for patients whose muscle around the knee joint is weak, such as an elderly person, the inferior end 24b of the first convex curved portion 24 is preferably positioned under the superior end 36t of the post 36 when a flexion angle is 0°. This arrangement can prevent the dislocation of the femoral component 20 in the anterior direction even at the flexion angle of 0°.

Second Embodiment

In the first embodiment of the invention, in order to increase the flexibility in rotation of the knee joint at the third engagement 5, the second sliding surface 25 of the femoral component 20 is formed as the spherical concave curved surface, and the fourth sliding surface 35 of the tibial plate 30 is formed as the spherical convex curved surface.

In contrast, a second embodiment of the invention differs from the first embodiment in that another means is provided to increase the flexibility in rotation of the knee joint.

Figure 14:
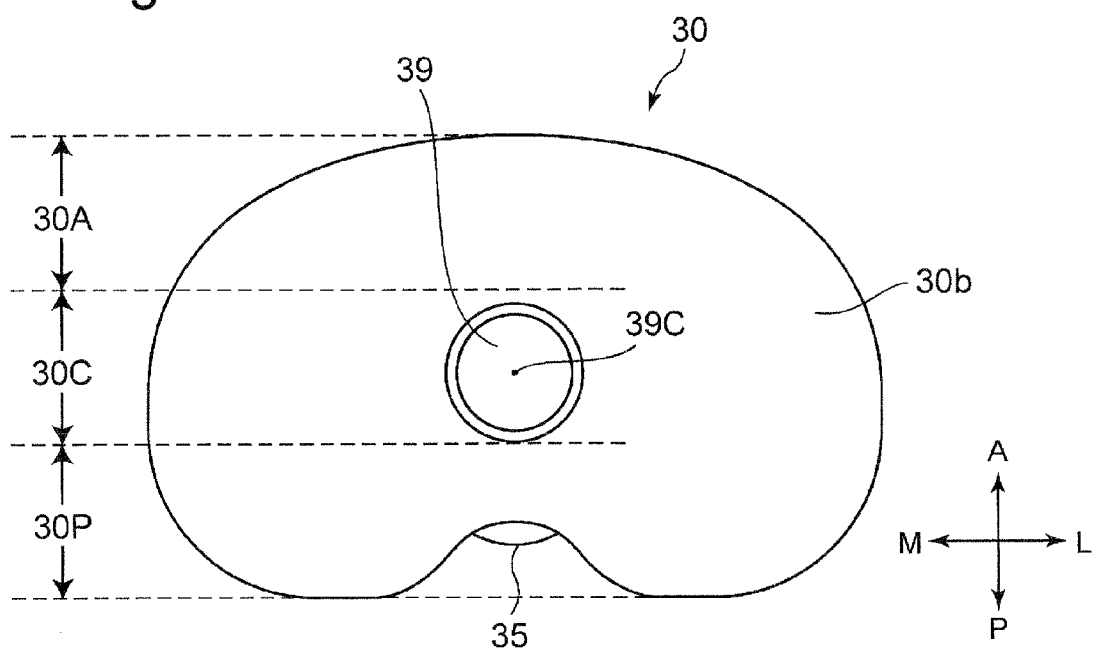
FIG. 14 is a bottom view of a tibial plate according to a second embodiment of the present invention.
Figure 15:
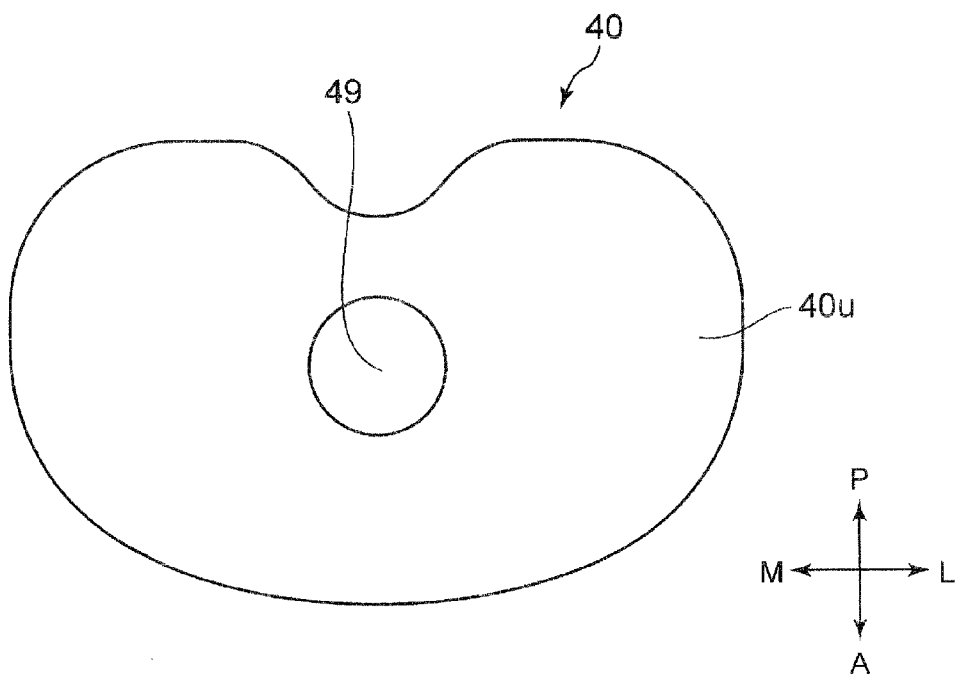
FIG. 15 is a top view of a tibial tray in the second embodiment.

In the second embodiment, the tibial plate 30 is rotatably engaged on the tibial tray 40. Specifically, as shown in FIG. 14, a cylindrical convex portion 39 is formed at an inferior surface 30*b* of the tibial plate 30. As shown in FIG. 15, a concave portion 49 is formed at a superior surface 40*u* of the tibial tray 40 to accept the convex portion 39. Such engagement between the convex portion 39 and the concave portion 49 is referred to as a "rotation engagement 6". The tibial plate 30 can rotate with respect to the tibial tray 40 with an axis center 39C of the convex portion 39 set as the center thereof. As a result, the femoral component 20 positioned on the superior side of the tibial plate 30 can also rotate with respect to the tibial tray 40. In this way, the rotation engagement 6 can be formed to rotate the artificial knee joint 1.

Figure 16:
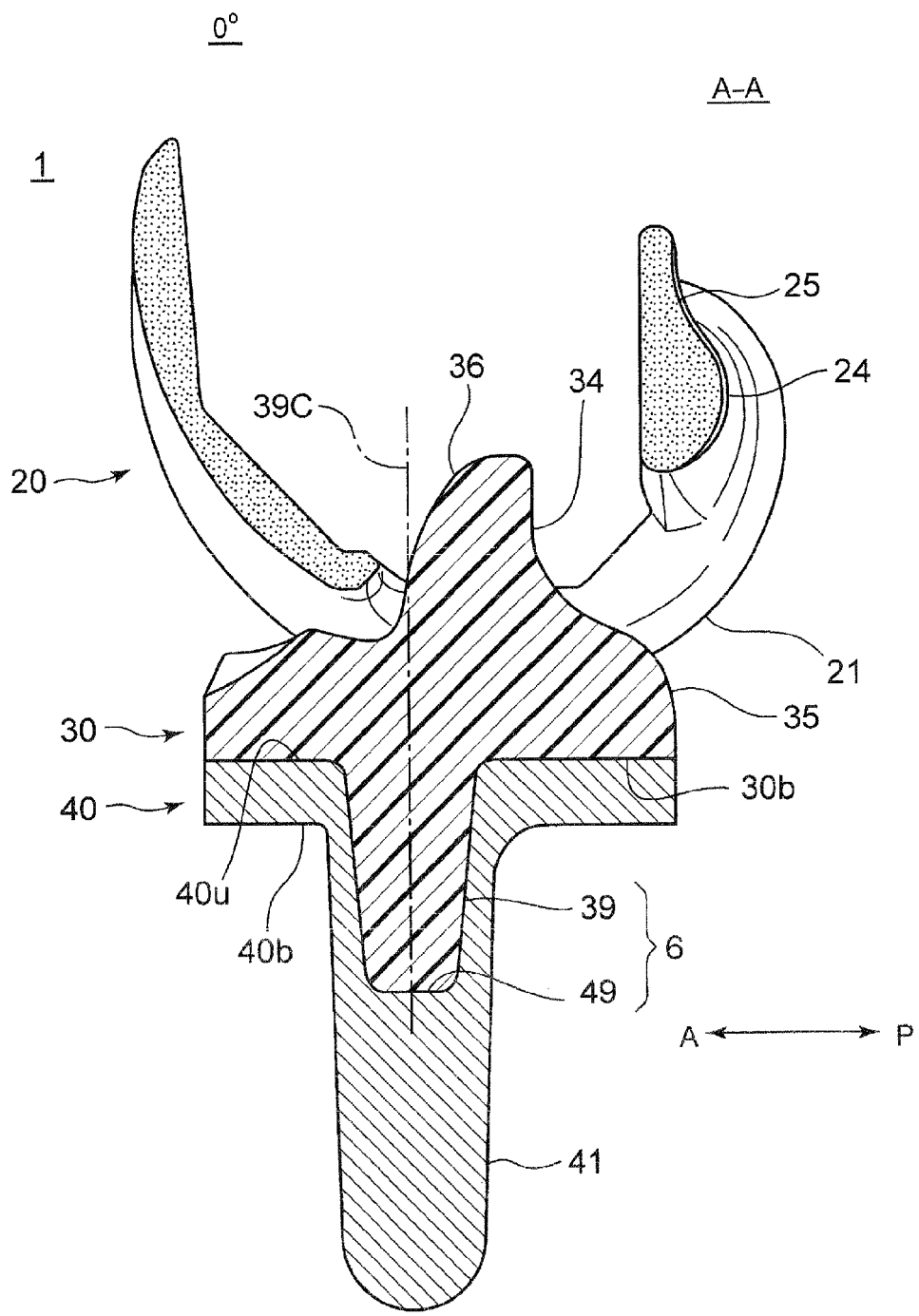
FIG. 16 is a cross-sectional view of the artificial knee joint in the second embodiment.
Figure 17:
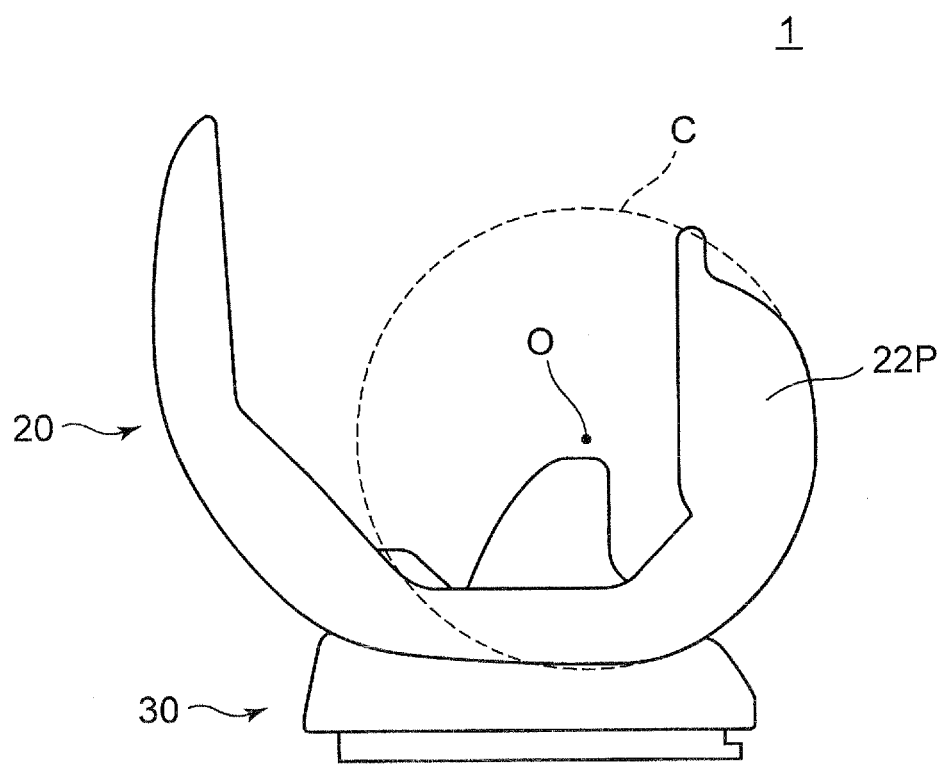
FIG. 17 is a cross-sectional view showing a method for approximating a posterior condyle of the femoral component of the artificial knee joint by a circle.

The cylindrical convex portion 39 can be shaped as a tapered convex portion 39 whose diameter is decreased downward as shown in FIG. 16.

When the artificial knee joint 1 includes the rotation engagement 6, the third engagement 5 itself may not have the rotation function. A part of the second convex curved portion 35 of the tibial plate 30 can be formed of a cylindrical member having an axis in the medial-lateral direction (M-L direction), and the first concave curved portion 25 of the femoral component 20 can be formed of a curved surface that accepts the cylindrical member.

The rotation engagement 6 enables the rotation in any one of the states in the first engagement 3, the second engagement 4, and the third engagement 5. The rotatability of the artificial knee joint in deep flexion (for example, at an angle of 150° to) 180° is preferably high in the same manner as the natural knee. For example, the rotation binding portion 6 is formed posteriorly, which can enhance the rotatability in the deep flexion.

When the rotation coupling portion 6 rotates, a posterior part of the tibial plate 30 and a posterior part of the femoral component 20 move in the medial direction with respect to the tibial tray 40. The excessive movement of the posterior parts in the medial direction makes the movement of the knee joint unnatural, which is not preferable. The movement in the medial direction increases as the rotation coupling portion 6 is placed posteriorly.

Taking into consideration the rotatability in deep flexion, and the movement in the medial direction in rotation, the rotation coupling portion 6 is preferably positioned in a center region 30C which is the central one of three regions (anterior region 30A, center region 30C, and posterior region 30P shown in FIG. 14) into which the tibial tray is divided in the anteroposterior direction. More specifically, an axis center 39C of a convex portion 39 of the tibial plate 30 is preferably positioned within the center region 30C.

The axis center 39*c* is positioned anteriorly within the center region 30C, which suppresses the rotatability of the rotation coupling portion 6 to thereby stabilize the operation of the femoral component 20 in the rotation direction with respect to the tibial tray 40. For example, when applied to patients whose muscle around the knee joint is weak, (such as an elderly person), the axis center 39C can also be located anteriorly.

Example 1

Figure 13:
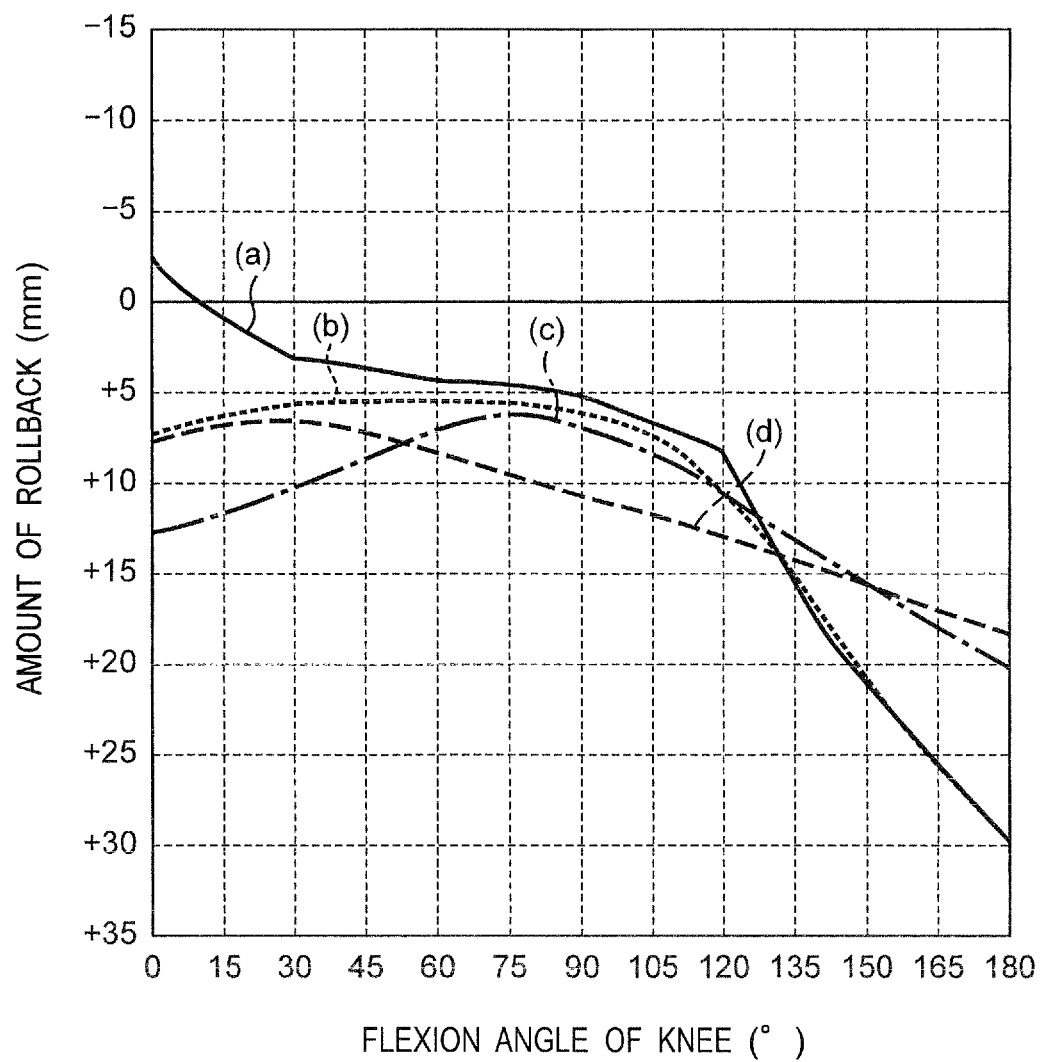
FIG. 13 shows graphs obtained by plotting the rollback amounts of the posterior condyles of the natural knee and the artificial knee joint against flexion angle, in which FIG. 13(a) indicates a graph of the natural knee, FIG. 13(b) indicates a graph of the artificial knee joint in the first embodiment, and FIGS. 13(c) and (d) are graphs of conventional artificial knee joints.

FIG. 13 is a graph obtained by plotting the rollback amounts of the artificial knee joint and the natural knee with respect to the flexion angle of the knee by simulation.

The rollback amount takes a positive sign (+) obtained when the center O of the posterior condyle moves posteriorly, and a negative sign (−) obtained when the center O moves anteriorly.

When the increase in flexion angle of the knee increases the rollback amount (that is, the center O of the posterior condyle moves posteriorly), the sign of the rollback ratio is positive (+). When the increase in flexion angle of the knee decreases the rollback amount (that is, the center O of the posterior condyle moves anteriorly), the sign of the rollback ratio is negative (−). The rollback ratio is identical to a slope of a tangent line of the graph obtained by plotting the rollback amounts against the flexion angle.

FIG. 13(*a*) is a graph showing the rollback amounts of the natural knee. When the flexion angle is between 30° and 90°, the line of the graph is substantially horizontal. When the flexion angle is between 90° and 120°, the line has a small positive slope. When the flexion angle is between 120° and 180°, the line has a large positive slope. The boundary between zone 1 and zone 2 estimated from the graph is at an angle of 110°.

FIG. 13(*b*) is a graph showing the rollback amounts of the artificial knee joint 1 of the first embodiment. The graph of the artificial knee joint is similar to that of the normal knee (see FIG. 13(*a*)). When the flexion angle is between 0° and 90°, the line is substantially horizontal. When the flexion angle is between 90° and 120°, the line has a small positive slope. When the flexion angle is between 120° and 180°, the line has a large positive slope. The boundary between zone 1 and zone 2 estimated from the graph is at an angle of 110°, similar to the natural knee.

FIGS. 13(*c*) and 13(*d*) are graphs of a conventional artificial knee joint. In FIG. 13(*c*), at a flexion angle of 0° to 70°, the line has a small negative slope. When a flexion angle is between 70° and 175°, the line has a small positive slope. An inflection point of the graph is at a flexion angle of 70°.

In FIG. 13(*d*), the line has a small negative slope at a flexion angle between 0° and 30°. The line has a small positive slope at a flexion angle between 30° and 180°. An inflection point of the graph is at a flexion angle of 30°.

As can be seen from FIG. 13, the artificial knee joint of the invention (see FIG. 13 (*b*)) is similar to the natural knee joint (see FIG. 13(*a*)) in slope of the graph, an angle formed at the boundary between zone 1 and zone 2, and the like. The artificial knee joint 1 of the invention can be found to appropriately reproduce the movement of the natural knee joint as compared to the conventional artificial knee joint.

The invention claimed is:

1. An artificial knee joint, comprising:
   a femoral component configured to be fixed to a distal part of a femur;
   a tibial tray configured to be fixed to a proximal part of a tibia; and
   a tibial plate engaged on the tibial tray in such a manner that the femoral component is movable relative to the tibial plate so as to change a flexion angle between the femoral component and the tibial plate, the femoral component comprising:
  a medial condyle;
  a lateral condyle;
  a first sliding surface coupling a posterior end of the medial condyle and a posterior end of the lateral condyle while leaving an opening between the medial condyle and the lateral condyle; and
a second sliding surface extending superiorly from the first sliding surface in such a manner that the second sliding surface is positioned directly above the first sliding surface when the flexion angle is 0°, and
the tibial plate comprising:
  a medial fossa configured to accept the medial condyle;
  a lateral fossa configured to accept the lateral condyle;
  a post protruding superiorly from between the media fossa and the lateral fossa, and configured to be inserted into the opening;
  a third sliding surface formed at a posterior surface of the post, the first sliding surface being configured to rotatably and slidably contact the third sliding surface; and
  a fourth sliding surface formed posterior to the post, the second sliding surface being configured to rotatably and slidably contact the fourth sliding surface,
the first sliding surface and the fourth sliding surface being convex curved surfaces,
the fourth sliding surface being positioned posterior to the third sliding surface,
wherein, according to the flexion angle, the femoral component and the tibial plate are configured to move in a first sliding state in which the first sliding surface and the third sliding surface are in contact with each other, or a second sliding state in which the second sliding surface and the fourth sliding surface are in contact with each other.

2. The artificial knee joint according to claim 1, wherein the femoral component and the tibial plate are configured such that the flexion angle at which the femoral component and the tibial plate transition from the first sliding state to the second sliding state is in a range of 75° to 155°.

3. The artificial knee joint according to claim 1, wherein the second sliding surface is a concave curved surface.

4. The artificial knee joint according to claim 1, wherein the second sliding surface is a spherical concave curved surface, and
wherein the fourth sliding surface is a spherical convex curved surface.

5. The artificial knee joint according to claim 1, wherein the third sliding surface is a concave curved surface.

6. The artificial knee joint according to claim 1, wherein the tibial plate is rotatably engaged on the tibial tray.

7. The artificial knee joint according to claim 1, wherein the flexion angle is between 45° and 150° in the first sliding state, and the flexion angle is between 150° and 180° in the second sliding state.

8. The artificial knee joint according to claim 1, wherein the medial condyle is not in contact with the medial fossa and the lateral condyle is not in contact with the lateral fossa in the second sliding state.

9. The artificial knee joint according to claim 1, wherein the flexion angle at which an inferior end of the first sliding surface is positioned under a superior end of the post is 30°.

10. The artificial knee joint according to claim 1, wherein the flexion angle at which an inferior end of the first convex curved surface is positioned under a superior end of the post is 0°.

11. The artificial knee joint according to claim 1, wherein the fourth sliding surface is disposed between the medial fossa and the lateral fossa.

12. The artificial knee joint according to claim 1, wherein the second sliding surface is continuous with the first sliding surface.

13. The artificial knee joint according to claim 1, wherein the first sliding surface and the second sliding surface are positioned directly above the opening.

14. The artificial knee joint according to claim 1, wherein a superior end of the second sliding surface is positioned superiorly beyond a superior end of the medial condyle and a superior end of the lateral condyle.

* * * * *